US00PP10119P

United States Patent [19]

Nagase

[11] Patent Number: Plant 10,119

[45] Date of Patent: Nov. 11, 1997

[54] TORENIA PLANT 'SUNRENIBU'

[75] Inventor: Yuki Nagase, Seki, Japan

[73] Assignee: Suntory Limited, Osaka, Japan

[21] Appl. No.: 559,853

[22] Filed: Nov. 20, 1995

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—Morgan & Finnegan; Eugene Moroz; Mary J. Morry

[57] ABSTRACT

A new and attractive hybrid of Torenia plant, named 'Sunrenibu', attained as selected superior hybrid seedling from a cross involving 'Crown Mix'×'Con Color'. The new plant has a less decumbent, more ascending or semi-upright habit, moderate branching and an unusually dense canopy of an attractive mounded form which does not collapse during the season. This plant produces a profusion of flowers of petals and corolla of a nearly monochromatic light purple; and has a high resistance to heat, moderate resistance to pests and diseases and is highly shade tolerant to produce copious flowers from about late June to November, or until killed by frost.

3 Drawing Sheets

BACKGROUND OF THE VARIETY

The present invention relates to a new and distinct variety of Torenia plant obtained from crossing "Crown Mix" (♀) and "Con Color" (♂).

The torenia is a very popular plant and is used for flower bedding and potting in the summer season. There are only a few varieties of the torenia plant which have a semi-erect growth habit, a high resistance to heat and diseases. And the Torenia plant needs full sunshine and hardly grows and has flowers in the shade of trees. Accordingly, this invention was aimed at obtaining a new variety having a great profusion of flowers, vivid purple flower petal with light purple floral tube, semi-erect growth habit, a high resistance to heat and diseases, and growing and having flowers ordinarily in the shade of trees.

The new variety of Torenia plant according to this invention originated from crossing "Con Color" as pollen parent and "Crown Mix" having white flower petals as female parent.

This new variety is an interspecific hybrid from within the genus Torenia.

This plant was originated as a seedling selection from a population of 30 seedlings resulting from the crossing of 'Con Color'×'Crown Mix'. The cross was effected in the spring of 1991 in the Plant Biotechnology Laboratory, Institute for Fundamental Research of SUNTORY Ltd., located at 1-1, Wakayamadai 1-chrom, Shimamoto-cho, Mishima-gun, Osaka-fu, Japan. The 30 siblings were forced to a transplant stage in the laboratory, then set out in beds and pots for trials beginning in the fall of 1991. The seedlings were systematically evaluated against the parent varieties for novel and useful traits, leading to the selection and isolation of the subject plant of this invention. In the tests, it has been concluded that this plant has a valuable combination of traits and is distinguishable from all other varieties of Torenia known to us. The plant was then asexually reproduced, by the taking and rooting of cuttings at the location noted above. Clonal progeny from such cuttings were observed to be uniform and stable, and have been identical to the initially selected plant in all distinguishing characteristics. Based on the discovery and testing of this plant, we have determined that this plant not only has a highly desirable shape, plant density, flower size and color characteristics, but has an unusually high tolerance of heat and flowers well in shaded garden conditions. It has been named 'Sunrenibu'.

In the following description, the color-coding is in accordance with the Horticultural Color Chart of The Royal Horticultural Society, London, England (R.H.S. Color Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

The female parent used in the crossing of this new variety "Sunrenibu" was "Crown Mix" having white flower petals is one of the Crown Series bred by the Sakata Seed Corp., Japan. The Crown Series includes plant having purplish blue flower petals, hi-color of white and purplish blue and the like, and these plants are commonly characterized by a high resistance to heat and are on the market in Japan. The main botanical characteristics of "Crown Mix" are as follows.

Plant:

*Growth habit.*—Erect.

*Plant height.*—20–30 cm.

*Plant extension.*—30–50 cm.

Stem:

*Diameter.*—3.0 mm.

*Anthocyanin pigmentation.*—Present.

*Branching.*—Few.

*Pubescence.*—Few.

*Length of internode.*—1–3 cm.

Leaf:

*Phyllotaxis.*—Opposite.

*Shape of blade.*—Serrate.

*Length.*—2.0–4.0 cm.

*Width.*—2.0–3.0 cm.

*Depth of incision.*—Deep.

*Color.*—Moderate olive green(R.H.S. 137A, JHS 3508).

*Pubescence.*—Few.

Flower:

*Facing direction.*—Laterally.

*Diameter.*—2.0–3.0 cm.

*Height.*—20–30 mm.

*Color of floral tube.*—Purplish white (R.H.S. 62D, JHS 8001).

*Color of petal.*—Single color, Purplish white (R.H.S. 62D, JHS 8001).

*Yellow eye color.*—Present. Vivid yellow (R.H.S. 17C, JHS 2507).
*Calyx.*—1.5–2.0 cm in length.
*Anthocyanin pigmentation of calyx limb.*—Present.
*Peduncle.*—1.5–2.0 mm in thickness; and 1.5–2.0 cm in length.
*Reproductive organs.*—1 pistil and 4 stamens.
*Anther color.*—White.
*Flowering duration.*—Medium.

Physiological and ecological characteristics: Low resistance to diseases and pests, high tolerances to heat and low tolerance to cold.

"Con Color" , used as the male parent in the crossing of this new variety "Sunrenibu", is one of the Con Color Series bred by the Sakata Seed Corp., Japan. The Con Color Series includes plant having violet flower petal, bi-color of storing purple and Pale purple and the like, and these plants are commonly characterized by a high resistance to heat and are on the market in Japan. The main botanical characteristics of "Con Color" are as follows.

Plant:
*Growth habit.*—Decumbent.
*Plant height.*—10–15 cm.
*Plant extension.*—50–70 cm.

Stem:
*Diameter.*—1.5 mm.
*Anthocyanin pigmentation.*—Present.
*Branching.*—Many.
*Pubescence.*—Few.
*Length of internode.*—4–6 cm.

Leaf:
*Phyllotaxis.*—Opposite.
*Shape of blade.*—Crenate.
*Length.*—1.0–2.0 cm.
*Width.*—1.0–2.0 cm.
*Depth of incision.*—Medium.
*Color.*—Moderate olive green (R.H.S. 137A, JHS 3508).
*Pubescence.*—Few.

Flower:
*Facing direction.*—Laterally.
*Diameter.*—2.0–3.0 cm.
*Height.*—20–30 mm.
*Color of floral tube.*—Moderate Purple (R.H.S. 83B, JHS 8613).
*Color of petal.*—Single color; Deep purple (R.H.S. 89C, JHS 8311).
*Yellow eye color.*—Absent.
*Calyx.*—1.5–2.0 cm in length.
*Anthocyanin pigmentation of calyx limb.*—Present.
*Peduncle.*—1.5–2.0 mm in thickness; and 3.0–5.0 cm in length.
*Reproductive organs.*—1 pistil and 4 stamens.
*Anther color.*—White.
*Flowering duration.*—Medium.

Physiological and ecological characteristics: High resistance to diseases and pests, high tolerances to heat and low tolerance to cold.

SUMMARY OF THE VARIETY

The new variety of torenia plant has a semi-erect habit, vivid purple flower petals with light purple floral tube without yellow eye color, and thus is very different from a similar variety, "Crown Violet" and "Con Color" .

The plant has semi-erect habit, medium branching and great profusion blooms, and the whole bush remains in bloom for a considerable period of time. The plant has a high resistance to heat, moderate resistance to diseases and pests, and grows and has flowers ordinarily in the shade of trees.

DESCRIPTION OF THE VARIETY

Figure 1:
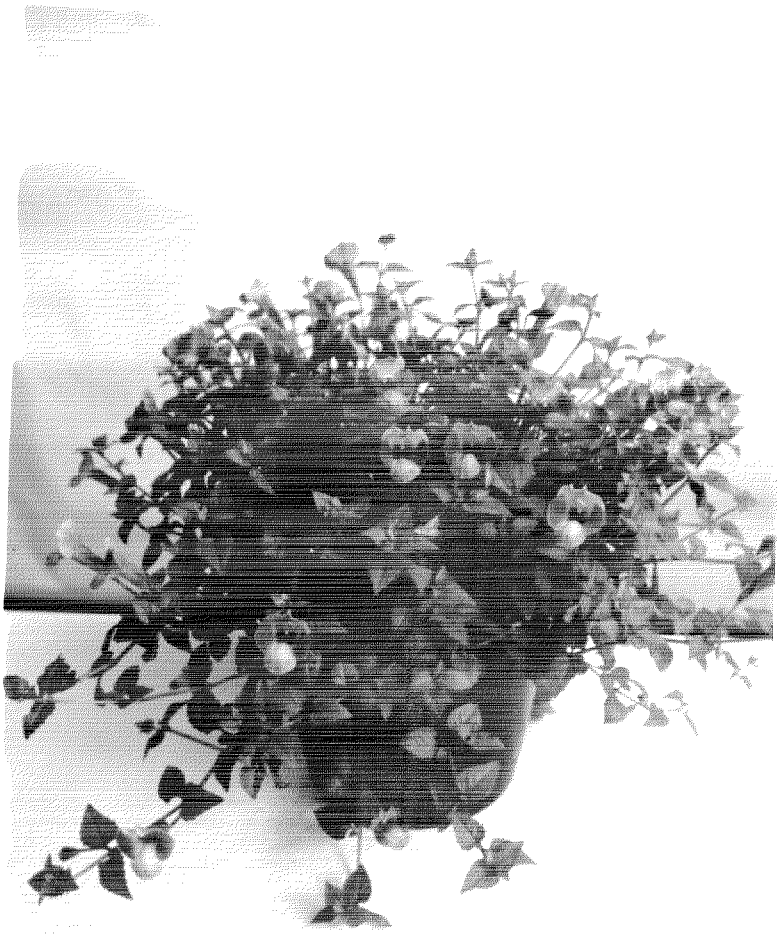
FIG. 1 is a photograph giving a partial view of the new variety of torenia plant planted in a flower pot.
Figure 2:
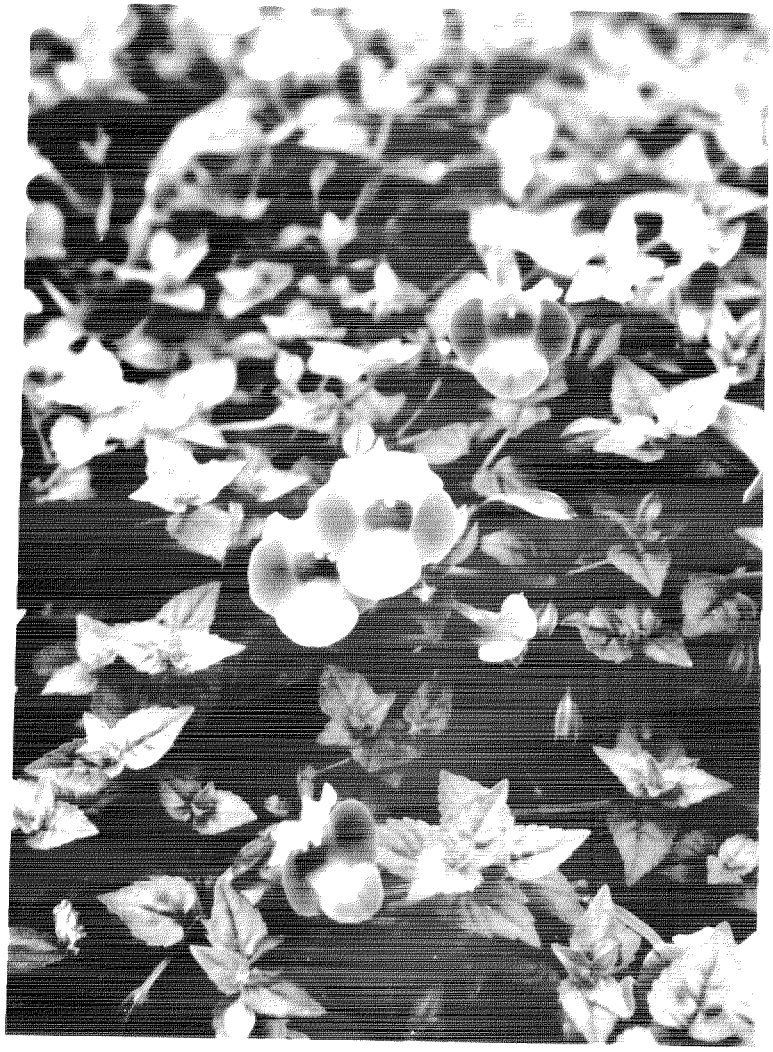
FIG. 2 is a photograph of flowers of the new variety of torenia plant.
Figure 3:
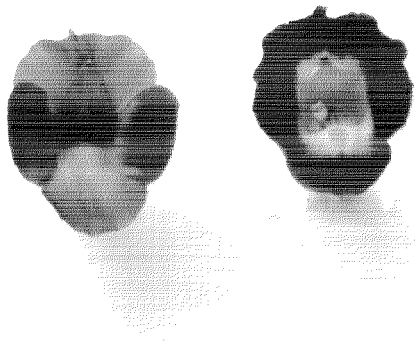
FIG. 3 is a photograph of flowers of the new variety of torenia plant, Sunrenibu (on the left) and the Crown Violet variety (on the right).

The botanical characteristics of the new and distinct variety of torenia plant "Sunrenibu" are as follows.

Plant:
*Growth habit.*—Semi-erect. The stems hang down pliantly when potted in a hanging pot.
*Plant height.*—15–20 cm.
*Plant extension.*—50–70 cm. The stem extends to length of 70 cm from the base.
*Growth.*—Medium branching, a great profusion of blooms; the whole bush remaining in bloom for a considerable period of time.
*Blooming period.*—June to November in the southern Kanto area, Japan. The plant shape does not change throughout this period.

Stem:
*Diameter.*—2.0 mm.
*Anthocyanin pigmentation.*—Present.
*Branching.*—Medium.
*Pubescence.*—Few.
*Length of internode.*—4—6 cm.

Leaf:
*Phyllotaxis.*—Opposite.
*Shape of blade.*—Serrate.
*Length.*—1.0–3.0 cm.
*Width.*—1.0–2.0 cm.
*Depth of incision.*—Medium.
*Color.*—Moderate olive green (R.H.S. 137A, JHS 3508).
*Pubescence.*—Few.

Flower:
*Facing direction.*—Laterally.
*Diameter.*—2.0–3.0 cm.
*Height.*—20–30 mm.
*Color of floral tube.*—Light purple (R.H.S. 92B, JHS 8303 ) .
*Color of petal.*—Single color; Vivid purple (R.H.S. 89B, JHS 8607).
*Yellow eye color.*—Absent.
*Calyx.*—1.5–2.0 cm in length.
*Anthocyanin pigmentation of calyx limb.*—Present.
*Peduncle.*—1.5–2.0 mm in thickness; and 2.0–3.0 cm in length.
*Reproductive organs.*—1 pistil and 4 stamens.
*Anther color.*—White.
*Flowering duration.*—Medium.

Physiological and ecological characteristics: Medium resistance to diseases and pests, high tolerances to heat and low tolerance of cold. The plant grows and has flowers ordinarily in the shade of trees.

This new variety "Sunrenibu" of torenia plant is most suitable for flower bedding and potting, particularly in hanging pots or planters.

This new variety "Sunrenibu" was asexually reproduced by cutting.

The plant of this new variety "Sunrenibu" is presently planted and maintained at the Nursery Center of the Plant Biotechnology Laboratory, Institute for Fundamental Research of SUNTORY Ltd., residing at 2913-1 Torihara, Hakushu-cho, Kitakoma-gun, Yamanashi-ken, Japan and the Plant Biotechnology Laboratory, Institute for Fundamental Research of SUNTORY Ltd., residing at 1-1, Wakayamadai 1-chome, Shimamoto-cho, Mishima-gun, Osaka-fu, Japan.

I claim:

1. A new and distinct variety of the Torenia plant, characterized as to novelty by its semi-erect habit, vivid purple flower petals with light purple floral tube without yellow eye color, substantially as shown and described.

* * * * *

3/3